(12) United States Patent
Roger et al.

(10) Patent No.: US 11,033,353 B2
(45) Date of Patent: Jun. 15, 2021

(54) FIDUCIAL MARKER

(71) Applicant: Cryptych Pty Ltd, North Sydney (AU)

(72) Inventors: Gregory James Roger, Milsons Point (AU); Davor Saravanja, Roseville (AU)

(73) Assignee: SPINAL DEVELOPMENTS PTY LTD, A.T.F. THE SPINESR UNIT TRUST, North Sydney (AU)

( * ) Notice: Subject to any disclaimer, the term of this patent is extended or adjusted under 35 U.S.C. 154(b) by 771 days.

(21) Appl. No.: 15/511,111

(22) PCT Filed: Sep. 9, 2015

(86) PCT No.: PCT/AU2015/050532
§ 371 (c)(1),
(2) Date: Mar. 14, 2017

(87) PCT Pub. No.: WO2016/041001
PCT Pub. Date: Mar. 24, 2016

(65) Prior Publication Data
US 2017/0231715 A1      Aug. 17, 2017

(30) Foreign Application Priority Data

Sep. 15, 2014   (AU) ................................ 2014903672

(51) Int. Cl.
*A61B 90/00*      (2016.01)
*A61B 17/86*      (2006.01)
(Continued)

(52) U.S. Cl.
CPC .......... *A61B 90/39* (2016.02); *A61B 17/7032* (2013.01); *A61B 17/8605* (2013.01);
(Continued)

(58) Field of Classification Search
CPC ..... A61B 90/39; A61B 34/20; A61B 17/7032; A61B 17/8605; A61B 2034/2055;
(Continued)

(56) References Cited

U.S. PATENT DOCUMENTS 6,394,725 B1 * 5/2002 Dicke .................. F16B 35/065
                                                              411/188
2003/0163040 A1    8/2003 Gildenberg
(Continued)

FOREIGN PATENT DOCUMENTS

DE    202006010728 U1    9/2006
EP         0739182 B1   10/1996
(Continued)

*Primary Examiner* — Bo Joseph Peng
(74) *Attorney, Agent, or Firm* — Browdy and Neimark, PLLC (57) ABSTRACT

A fiducial marker and method for use in the navigation of a surgical procedure is described. The fiducial marker includes a means to readily guide a navigation probe and includes an upper surface with a sloped guide surface for guiding the probe, the upper surface further including a substantially centrally positioned well to receive at least part of the probe. The guide surface may alternatively be configured to align with a complementary portion of part of the navigation probe.

8 Claims, 6 Drawing Sheets

(51) Int. Cl.
*A61B 34/20* (2016.01)
*A61B 17/70* (2006.01)
*A61B 17/00* (2006.01)
*A61B 34/00* (2016.01)

(52) U.S. Cl.
CPC .............. *A61B 34/20* (2016.02); *A61B 34/25* (2016.02); *A61B 2017/00004* (2013.01); *A61B 2034/207* (2016.02); *A61B 2034/2055* (2016.02); *A61B 2090/3937* (2016.02); *A61B 2090/3966* (2016.02); *A61B 2090/3983* (2016.02); *A61B 2090/3991* (2016.02)

(58) Field of Classification Search
CPC .... A61B 2090/3937; A61B 2090/3983; A61B 2090/3991; A61B 2017/00004
See application file for complete search history.

(56) References Cited

U.S. PATENT DOCUMENTS

| | | | |
|---|---|---|---|
| 2004/0167391 A1* | 8/2004 | Solar | A61B 90/39 600/411 |
| 2005/0085714 A1* | 4/2005 | Foley | A61B 17/1735 600/424 |
| 2007/0016219 A1 | 1/2007 | Levine | |
| 2007/0233122 A1* | 10/2007 | Denis | A61B 17/7032 606/247 |
| 2010/0033388 A1 | 3/2010 | Solar et al. | |
| 2010/0298846 A1 | 11/2010 | Kao et al. | |
| 2013/0041228 A1* | 2/2013 | Gorek | A61B 17/02 600/204 |
| 2014/0005524 A1 | 1/2014 | Ulfarsson et al. | |
| 2016/0166335 A1 | 6/2016 | Roger | |

FOREIGN PATENT DOCUMENTS

| | | |
|---|---|---|
| WO | 1998036371 A1 | 8/1998 |
| WO | 2015003224 A1 | 1/2015 |

\* cited by examiner

FIDUCIAL MARKER

FIELD OF THE DISCLOSURE

The present disclosure relates to a device and system for use in surgery. The device and system aid in reliable navigation of the anatomical landscape.

BACKGROUND

Surgery, such as implant surgery and in particular spinal implant surgery, requires knowledge of the anatomy of the patient which can often be quite distorted through degeneration, deformity, neoplasia or trauma. An ability to navigate safely around the anatomy surgically throughout an entire procedure is also desirable.

While experience can allow a surgeon or surgical team to perform procedures without the assistance of aids, this experience can take some time to accumulate. In less experienced hands, as well as for more complex cases with grossly distorted anatomy, a number of systems have been devised to help make the surgery more reliable and safe. An example includes computer assisted surgery, in which a computer tomograph (CT) of an anatomical structure is used to assist the surgery.

In fields such as neurosurgery the use of fiducial markers, attached to the patient prior to a scan being performed, has become commonplace. In the context of intracranial neurosurgery the movement of the neural tissue with reference to the fiducial markers attached to the skull is minimal. As a consequence these pre-operative scans can be performed in dedicated radiology departments with sophisticated high resolution scanning equipment. The navigation equipment in the operating theatre can then be registered to these 3D images and the information therein used during surgery.

In surgery on, for example, the spine, however, there are less accessible bony landmarks for insertion of fiducial screws. Further, and importantly, pre-operative scans are not reliable due to the significant relative motion inherent in the vertebral elements of a spinal column.

As a result, in spinal surgery, scans are performed once the patient is positioned on the operating table and the spinal column has been operatively exposed. This allows navigation equipment to be attached to a nearby bony structure so that a mobile CT scanner can scan both the spine and the navigation equipment with the resultant images fed to a navigation system to allow guidance during surgery.

Despite the fact that the patient is positioned on an operating table and is relatively motionless, there is nevertheless motion between the vertebrae. This can be caused by respiration, movement of the table itself, motion caused by retractors and other surgical instruments and inadvertent disturbance of the navigational equipment by the surgical team.

As a consequence fiducial markers are desirable in spinal surgery, not to orient the scans to the patient as occurs in neurosurgery, but rather to allow confirmation of the accuracy of the navigation information as the surgery progresses. Such fiducial markers can be temporarily inserted onto one or more vertebrae and can also be inserted into bone that is to be removed surgically. The role of the markers is to check local accuracy rather than being part of the overall navigation system.

There are a number of surgical difficulties associated with the intra-operative use of fiducial markers including ease and accuracy of imaging the marker, ease of engagement with a navigating probe with the markers and ease of insertion of the markers into the vertebral bone.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In a first aspect, there is provided a fiducial marker comprising:
 a head having an upper surface and a lower surface;
 a shaft extending along a longitudinal axis from the lower surface of the head;
 the upper surface having a sloped guide surface for guiding a navigation probe, the upper surface further including a substantially centrally positioned well to receive at least part of the navigation probe.

In a second aspect, there is provided a fiducial marker comprising:
 a head having an upper surface and a lower surface;
 a shaft extending along a longitudinal axis from the lower surface of the head;
 the upper surface having a guide surface for receiving a navigation probe, the guide surface configured to align with a complementary portion of at least part of the navigation probe.

In one embodiment of both the above aspects, the fiducial marker comprises a fiducial screw. The fiducial marker may also comprise a pedicle screw. Alternatively, at least the upper surface and well features described may form part of another implant or a surgical tool.

In the embodiment of both aspects wherein the fiducial marker comprises a pedicle screw, during insertion into a bone of a patient the pedicle screw may be registered on a navigation system and subsequently probed with the navigation probe to re-register its position throughout a surgical procedure.

The guide surface of the first aspect typically slopes from an outer edge of the head, inwardly and downwardly towards the shaft to an inner edge which defines the opening of the well.

The head may include a depth from an upper edge of the upper surface to a lowest point on the lower surface. The depth of the head may vary depending upon the application of the screw including the type of surgery and depth of bone.

In relation to the first aspect, the opening of the well of the head is typically defined by the inner edge of the guide surface and may be substantially centrally located on the head. The well may include at least one sidewall extending from an uppermost edge towards the lower surface of the head. The well further includes a closed base. A depth of the well is taken as the distance between the uppermost edge of the sidewall and the closed base.

The diameter of the well may be less than 30% of the diameter of the head. In embodiments, the diameter of the well may be 25% or less than the diameter of the head; 20% or less than the diameter of the head; 15% or less than the diameter of the head; 10% or less than the diameter of the head; 5% or less than the diameter of the head. In some embodiments, the diameter of the well may be 10% of the diameter of the head; 11% of the diameter of the head; 12% of the diameter of the head; 13% of the diameter of the head; 14% of the diameter of the head; 15% of the diameter of the head; 16% of the diameter of the head; 17% of the diameter of the head; 18% of the diameter of the head; 19% of the diameter of the head; or 20% of the diameter of the head.

The diameter of the well may be between 0.5 mm and 2.0 mm. In one embodiment the diameter is between 1.0 mm and 1.5 mm. In a further embodiment, the diameter of the well is approximately 1.0 mm.

The at least one sidewall and base of the well may define a number of shapes to receive a probe. In one embodiment, the well is substantially hemispherical in shape. This embodiment may be useful when receiving a substantially spherically ended probe.

Alternatively, the at least one sidewall and base may define a substantially frustoconically shaped well. In another embodiment, the well may be U-shaped.

In one embodiment, the well is V-shaped, the one or more sidewalls meeting to form a pointed base.

The base of the well may be substantially curved or, alternatively, the base may be substantially planar.

The at least one sidewall of the well may comprise a continuous sidewall. The at least one sidewall may be substantially curved. Alternatively, the at least one sidewall may be substantially planar.

The well may be defined by a plurality of sidewalls. For example, in one embodiment, the well may be defined by three or four sidewalls. In a further embodiment, the well may be defined by five sidewalls; six sidewalls, seven sidewalls, eight sidewalls, nine sidewalls or ten or more sidewalls. In a preferred embodiment, the well is defined by six sidewalls to form a hexagonally shaped recess in the head. Each side wall may be substantially curved or alternatively, each sidewall may be substantially planar.

The shape defined by the well may substantially match with the shape of the guide surface of the upper surface. For example, if the well is a substantially hemispherical structure, the guide surface may define a similarly hemispherical structure. Where the well includes a plurality of sidewalls, the guide surface may include an equivalent number of faces on the upper surface. Alternatively, the shape defined by the sidewall(s) of the well may differ to the shape of the guide surface.

The one or more sidewalls of the well may have a substantially steeper sloped pitch relative to the slope of an equivalent one or more faces of the guide surface. The pitch of the slope of the upper surface including the at least one sidewall of the well and the guide surface is taken to be the angle of the slope relative to an axis which is normal to the longitudinal axis of the shaft.

The pitch of the slope of the guide surface may be constant along a length of the guide surface from the outer edge of the guide surface to the inner edge. Alternatively, the pitch of the slope of the guide surface may vary along its length. Any variation in pitch of the guide surface slope is typically smooth and devoid of sharp transitions areas which may impede the smooth guidance of the probe.

The head may further comprise at least one outer sidewall extending between the upper surface and the lower surface. In one embodiment, the outer sidewall of the head may comprise a continuous cylindrical surface. Alternatively, the outer sidewall may comprise a plurality of sidewalls. For example, the at least one sidewall may comprise three sidewalls, four sidewalls, five sidewalls, six sidewalls, seven sidewalls, eight sidewalls, nine sidewalls or ten or more sidewalls. In a preferred embodiment, the head includes six outer sidewalls.

The at least one outer sidewall may be substantially planar. Alternatively the at least one outer sidewall may be substantially curved. The curvature of the at least one outer sidewall may be concave or convex.

The at least one outer sidewall may comprise a ribbed or roughened surface. Alternatively, the surface may be smooth.

In one embodiment, wherein the outer sidewall includes a hexagonal structure with six sidewalls forming a driver feature, a socket driver may be used to engage the hexagonal structure of the head and insert the marker into the bone. By having such driver features of the fiducial marker comprising an outer surface of the head, the guide surface and the well of the head are unencumbered by any such features. This allows a probe to be touched down on the guide surface and into the well without any impediment.

The at least one outer sidewall of the marker of the first aspect may include a threaded region. In this embodiment, it is envisaged that the head of the fiducial marker may be threadingly advanced into a bone such that the head is substantially counter-sunk in said bone.

The lower surface of the head typically includes a central portion substantially aligned longitudinally with the well of the head. The central portion typically includes the lowest point on the lower surface. Further, the shaft of the fiducial marker typically extends from the central portion of the lower surface. The lower surface may curve outwardly from the central portion to an outer portion which meets the at least one outer sidewall. The curvature of the lower surface may vary depending upon the bone in which the marker is positioned. The rate of curvature of the lower surface may be constant or, alternatively the rate of curvature may vary along the lower surface from the central portion to the outer portion.

A curved lower surface may allow the marker to be inserted into a bone at a number of angles other than at substantially right angles to the surface of the bone. The lower surface preferably has a degree of curvature to allow the marker to be inserted anywhere from 45° relative to the surface of a bone to 90° relative to the bone. Such curvature allows the head to sit on a bone despite having been introduced at an angle and such that the head does not present a significant prominence to cause a hazard in surgery or impede the use of other surgical equipment.

In another embodiment, the lower surface is substantially planar rather than curved.

In one embodiment, a junction is formed between a lower edge of one or more outer sidewalls and the outer portion of the lower surface. The depth of the well is the depth measured from an uppermost edge of the well, which meets the inner edge of the guide surface, to its closed base. The base of the well typically substantially aligns with the junction formed between the lower edge of the one or more outer sidewalls and the outer portion of the lower surface.

The outer sidewalls may be visible to a CT or other scanner in use, the sidewall being distinct from the lower curved surface of the head. In the embodiment wherein the depth of the well is such that the base aligns with the junction between the outer sidewalls and the lower surface a ready visual comparison of the location of the navigation probe in relation to the fiducial marker on the navigation system's imaging screens is provided. If the probe is accurately shown on a screen it will appear to be centrally positioned on the head and at the same depth as the junction of the outer walls and the lower surface.

In one embodiment of the second aspect, the guide surface provides a convex surface to receive a complementary concave surface of the navigation probe. In one embodiment, the guide surface may be partially spherical. The guide surface may comprise a hemispherical surface.

The guide surface may comprise only part of the upper surface. Typically, however, substantially all of upper surface comprises a convex surface to receive a complementary concave surface of the navigation probe.

The upper surface may extend to a join with the lower surface. Alternatively, the head of the marker of this aspect may also include at least one outer sidewall extending between the upper surface and the lower surface.

In one embodiment, the outer sidewall of the head may comprise a continuous cylindrical surface. Alternatively, the outer sidewall may comprise a plurality of sidewalls. For example, the at least one sidewall may comprise three sidewalls, four sidewalls, five sidewalls, six sidewalls, seven sidewalls, eight sidewalls, nine sidewalls or ten or more sidewalls. In a preferred embodiment, the head includes six outer sidewalls.

The at least one outer sidewall may be substantially planar. Alternatively the at least one outer sidewall may be substantially curved. The curvature of the at least one outer sidewall may be concave or convex.

The at least one outer sidewall may comprise a ribbed or roughened surface. Alternatively, the surface may be smooth.

At least a portion of the head of the fiducial marker of the second aspect may include an external thread. In this embodiment, the head of the fiducial marker may be at least partially countersunk into a target bone.

The lower surface of the head of this aspect may extend from a join with the shaft of the fiducial marker to a join with the upper surface. The lower surface may be substantially planar such that the head sits flat on a bone in which the marker is inserted.

The upper surface may include a drive portion to receive part of a suitable driver to allow the fiducial member to be driven into the bone. The drive portion may comprise a hexagonal socket to receive a hex key or Allen key. Alternatively, the drive portion may comprise crossed recesses to receive a driver member.

In a further embodiment of the second aspect, the guide surface may comprise a plurality of recesses in the upper surface. The plurality of recesses may receive complementary protrusions on part of the navigation probe. The guide surface may comprise one, two three, four or more recesses to receive complementary protrusions therein.

The following description relates to features of the fiducial markers of both the first and second aspects.

The shaft of the marker is typically threaded along at least part of its length. The entire length of the shaft may be threaded. In one embodiment the shaft includes a self drilling and/or self tapping thread. In a further embodiment the thread has a reduced depth adjacent to the lower surface of the head such as to increase grip and stability in the bone without compromising the ability to insert the marker.

In a still further embodiment rather than a threaded shaft, the fiducial marker may include a surface texturing to secure the fiducial marker in bone. In this embodiment a filler material such as polymethylmethacrylate for example or a bio-degradable filler or adhesive may be used to secure the fiducial marker to the bone.

The fiducial marker may comprise a screw and be made from any suitable biocompatible material. The fiducial marker is typically of sufficient strength to be screwed into the bone and to be suitably imaged during a procedure. In one embodiment, the fiducial marker may be made from medical grade stainless steel. In a further embodiment, the fiducial marker may be made from titanium. The head and shaft may be made from the same or from a plurality of different materials. In one embodiment, the fiducial marker may be made from a resorbable material.

Part of the fiducial marker and/or the navigation probe may also be doped with a substance such as barium, titanium, iodine, silver, gold, platinum, titanium dioxide, to provide a contrast on a CT or other imaging system. In one embodiment at least a portion of the well may be doped with such a material. Additionally, or alternatively, another portion of the fiducial marker may be doped including the one or more outer sidewalls of the marker.

The fiducial marker may further include a region which is reflective of light or other electromagnetic energy. Alternatively, the fiducial marker may be connected to a reflective member such as one or more reflective balls. In one embodiment, the fiducial marker may include a coating or patch which is reflective of light or other electromagnetic energy. The coating or patch may be positioned on the outer sidewall(s) of the fiducial marker.

In another embodiment, the upper surface of the head may include a means for attracting a navigation probe. For example, part of the well including the at least one sidewall and/or the base may include a magnetised surface to attract a portion of the navigation probe.

The fiducial marker may also include a collar positioned along a region of the lower surface of the head or at a juncture between the lower surface of the head and the shaft. In one embodiment, the collar is cinched around the shaft at a first end of the shaft, connected to the lower surface of the head.

The collar is typically made of a suitable biocompatible material. In one embodiment, the collar includes a length of surgical thread. The collar may be made from a number of non-absorbable materials such as polypropylenes, polyamides, polyesters and silk. In another embodiment, the collar may be made from an absorbable material including polyglycolic acid sutures, polygalactin 910, catgut, and polydioxanone.

The collar may include a tail portion which extends outwardly from the marker. The tail may be up to 2 cm in length and more preferably up to 1 cm in length.

The collar is typically brightly coloured to allow easy visualisation to locate the fiducial marker, for example for removal of the marker from the bone.

The collar may be removably connected to the fiducial marker such that it may be removed if the marker is left in situ in the bone. Alternatively, the collar may be left connected to the marker in situ.

In a third aspect, there is provided a system for aiding surgery on a patient comprising:
  one or more fiducial markers each comprising a head having an upper surface and a lower surface; a shaft extending along a longitudinal axis from the lower surface of the head; the upper surface having a sloped guide surface to guide a navigation probe, the upper surface further including a substantially centrally positioned well to receive at least part of the navigation probe;
  a display device; and
  a storage device that stores an image of at least a portion of the anatomy of the patient, including, for display on the display device,
  an analyser adapted to receive positional data of a navigation probe based on positioning of the probe relative to one or more of said fiducial markers on the patient; and wherein, based on said positional data, said analyser outputs correctional data to adjust an alignment of the image on said display device to match locations of said one or more fiducial markers.

In a fourth aspect, there is provided a system for aiding surgery on a patient comprising:

one or a fiducial markers comprising:

a head having an upper surface and a lower surface;

a shaft extending along a longitudinal axis from the lower surface of the head;

the upper surface having a guide surface for receiving a navigation probe, the guide surface configured to align with a complementary portion of at least part of the navigation probe;

a display device; and a storage device that stores an image of at least a portion of the anatomy of the patient, including, for display on the display device, an analyser adapted to receive positional data of a navigation probe based on positioning of the probe relative to one or more of said fiducial markers on the patient; and wherein, based on said positional data, said analyser outputs correctional data to adjust an alignment of the image on said display device to match locations of said one or more fiducial markers.

The markers of the present disclosure may be used in a system such as disclosed in PCT/AU2014/050117, the contents of which are herein incorporated.

The present fiducial markers may be used in a number of surgical operations and systems for navigation and registering anatomical positions. By providing positional data and correctional data, a system can allow the alignment of a displayed image to be registered or re-registered with the patient during a surgical process. The fiducial markers are not limited to an initial navigation process during a surgery and may in fact be left in the body of a patient or used separately for further analysis. Such further analysis may include radio-stereometric analysis (RSA).

A system for navigating a surgery may include a display device and a storage device which stores an image of part of the anatomy of a patient. The system may also include an analyser to compare the image with the position of one or more fiducial markers positioned on the patient and provide an output of said comparison to the display device. The system may also include an input device capable of receiving data from the navigation probe which is positionable relative to said one or more fiducial markers and delivering said data to the analyser. The analyser may process the data and output correctional data that adjusts the alignment of the image on the display device to match with the location of said one or more fiducial markers.

The probe can, therefore, be used to identify positions of one or more fiducial markers herein disclosed and, following accurate registration, a displayed image on a display device and positional data from the navigation probe can be used to accurately update or introduce representations of the identified features in the displayed image. The surgical navigation can, therefore, be more accurate at any given time during surgery, notwithstanding any manipulation of the patient's anatomy that may have occurred.

The display device may comprise any display suitable for the purposes described herein. It may comprise, for example, a television screen, a computer monitor, a LED display, a hologram/holograph, a touch screen or a combination of such displays. The display device can comprise multiple display screens. It may also comprise one screen capable of displaying different images simultaneously or sequentially as required.

Positional data of the probe may be determined at least partially using a navigation device such as a camera, e.g. an infrared (IR) camera, which can monitor changes in position of the probe. The IR camera may provide a form of input device to the analyser.

The image may be provided by a computed tomography (CT) device, a MRI device and/or an X-ray device and/or any other means of generating scaleable images or representations of the anatomy.

For spinal surgery applications, to position the one or more fiducial markers, a surgeon may first expose the bony anatomy of the spine, posteriorly, laterally or anteriorly, at the desired levels. A first fiducial marker may then be mounted to a piece of bone away from the area to be resected or operated upon. Typically, this may be the adjacent vertebra on the spine.

One or more of the fiducial markers, such as the first marker may comprise or support one or more reflective components, such as reflective balls. The reflective components may be designed to reflect light of a particular frequency, for example infrared (IR), with a navigation device, such as an IR camera, having a capability to remotely detect the position of the fiducial markers and/or probe being then part of the system. Other surgical instrumentation including the navigation probe may also comprise or support similar reflective components for the purposes of position detection using the navigation device such as the IR camera. The IR camera is typically pointed at the entire operative site, including the fiducial markers mounted to bone.

Once the patient has been prepared as described above, the image, e.g. a CT scan, can then be taken. This can be achieved through use, for example, of a mobile CT scanner that is brought into the operating theatre. In taking the CT or other scan, the aim may be to show all of the desired operative levels as well as the fiducial markers. Two or more scans may therefore be taken at different anatomical levels. The scans may be combined to create a three dimensional image. The fiducial markers may be used as orientation points to ensure that the combined scans are appropriately aligned. By creating a three dimensional image in this manner, a surgeon or other practitioner may advance or scroll through different levels in the image as surgery proceeds along the spine or otherwise. The displayed image may therefore provide navigational information to the surgeon at different levels of the anatomy that is subject to the surgical procedure.

The scanner may be connected to and/or monitored by the IR camera and the subsequent images can then be looked at in all three planes simultaneously on three separate regions or windows of a relatively large output screen comprising the display device. Through the connection/monitoring, the system can determine the positioning of the scanner relative to the patient at the time of obtaining the images. The images typically show the patient as they are lying on the operating table at the time the scan is taken and the fiducial markers can be seen in the bone.

In the case of spinal surgery, the system may be used to identify the correct placement point for one or more pedicle screws, (and optionally also other surgical hardware or fixation devices) as well as the correct angle to drill for them. The pedicle screws may be adapted to support a spinal rod or otherwise. As the pedicles of the vertebra are drilled, the navigation probe can also be inserted into the drill hole to check its location and orientation. The planned screw size can also be superimposed, rather than just the line of the probe, to ensure the screw diameter does not exceed the available space.

During this procedure, the fiducial markers may be used, from time to time, to check the accuracy of the navigation. Because the fiducial markers are in situ when the scan is taken, they show on the scans. The navigation probe as superimposed on the displayed image should then be shown exactly on the scanned markers when the probe is touched onto the actual marker by the surgeon. However, this is often not the case, with the marker appearing to be up to 1 or more millimetres away from the position of the probe when viewed on the display device, despite the fact the probe is placed exactly on the fiducial marker, e.g. exactly in the head or in the well of the head or as the head design allows. This "offset" may require the surgeon to estimate a correction for the image shown for the other areas of anatomic interest, such as the pedicle of the vertebra.

There are many causes for this apparent "offset". A first fiducial marker (e.g. a marker comprising reflective componentry) may shift slightly due to softness of the bone that it is mounted on and/or by virtue of being knocked by a surgical instrument or one of the surgical team. Further, as the spine is realigned through surgical instrumentation or positioning of a movable operating table, the relative position of each vertebra to the vertebra on which the marker is mounted may shift. Likewise, image acquisition and hence navigation can be compromised by changing surgical retraction during a procedure, either during or after image acquisition.

The system as described herein provides the surgeon or surgical team with a means to be aware of the offsets and their magnitude and where possible correct for such offsets when they occur.

In one embodiment, correction is achieved through positioning one or more fiducial markers to the patient. At least three fiducial markers may be positioned on the patient, e.g. on each individual vertebra, and each aligned with a different anatomical axis/plane to that of the others. The use of at least three fiducial markers may ensure that the image can be realigned in all three axes/planes, so ensuring an appropriate three dimensional image of the anatomy of the patient. However, in general, alignment of the image to match with the location of one or more fiducial markers may be along any one or more axes.

In one embodiment, the analyser of the system can make an initial determination of the position of the fiducial markers and so form a three dimensional image. For example, the analyser can in effect create a three dimensional solid based on the initial determination of the fiducial markers. The surgeon may then use the navigation probe to physically touch the actual fiducial markers to generate positional data. The analyser can then use the positional data provided by this action to output correctional data and form a corrected three dimensional solid and then align the image on the screen to the actual location of the body.

In a further embodiment, a fourth or greater numbers of fiducial markers may be used to provide additional positional data to the analyser so providing improved accuracy. The output correctional data from the analyser and imagery generated can be stored by the system and can be retrievable so allowing the surgeon to revert to any earlier image should that be required.

The fiducial marker may be introduced into the bone by a socket driver. The socket driver may comprise a number of types of driver and in one embodiment may include an elongate body extending from a first end to a second end and having a two extending legs and a space therebetween. The two legs are typically made from a resiliently flexible material and may engage the one or more outer sidewall of the fiducial marker to grip the marker and allow for insertion into the bone. The driver may further include an outer sleeve which may extend over the two legs and tighten the engagement of the fiducial marker by the legs. This may be useful when introducing the fiducial marker into relatively hard bone.

BRIEF DESCRIPTION OF THE DRAWINGS

FIG. 10a is a cross sectional view through A-A of FIG. 10b showing a further embodiment; and FIG. 10b is a top plan view of the embodiment of FIG. 10a.

DESCRIPTION OF EMBODIMENTS

One embodiment of the fiducial marker is generally shown as 10 in the accompanying drawings. Fiducial marker 10 has a head 11 which has an upper surface 12 and a lower surface 13. Shaft 14 extends along a longitudinal axis from lower surface 13 of head 11.

Upper surface 12 has a sloped guide surface 15 to receive and guide a navigation probe 100. Well 16 is centrally positioned in the head 11 and configured to receive the end 101 of navigation probe 100.

Guide surface 15 extends from an outer edge 17 of head 11, inwardly and downwardly towards shaft 14. Guide surface 15 terminates at an inner edge 18 which defines the opening of well 16. Well 16 is positioned in a central part of head 11 and its upper opening is defined by the inner edge 18 of guide surface 15. Sidewall 20 extends from inner edge 18 to a closed well base 21.

The diameter of the well can be seen in the Figures to be significantly less than the diameter of head 11. The diameter should, however, be sufficient to receive the end 101 of probe 100.

Figure 1:
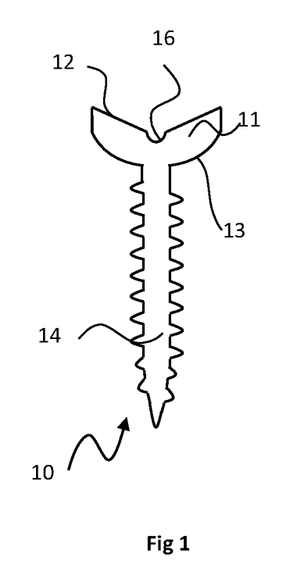
FIG. 1 is a side view of an embodiment of a fiducial marker.
Figure 2:
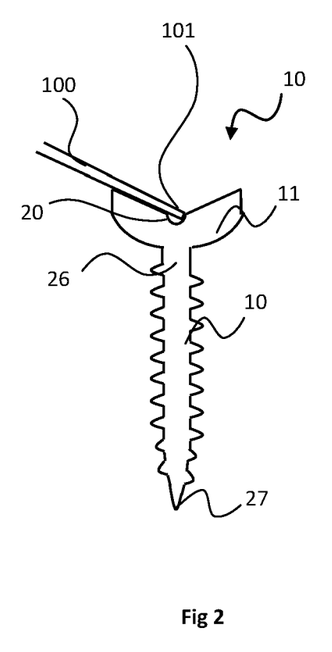
FIG. 2 is a side view of an embodiment of a fiducial marker with a probe touched against the well of the marker.
Figure 3:
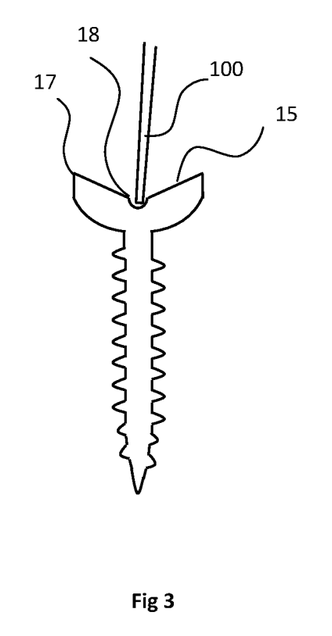
FIG. 3 is a side view of the embodiment of FIG. 2 with the probe orientated differently.

In FIGS. 1 to 3, the well is substantially hemispherical in shape. However, other shapes are envisaged. Further, the slope of the sidewall 20 of well 16 may vary and may be more or less sloped than depicted. However, it is envisaged that the slope is sufficient to prevent end 101 of probe 100 slipping out of the well in use.

The sidewall 20 of the well as shown in FIGS. 1 to 3 and FIG. 6 has a steeper pitched slope relative to the pitch of the slope of guide surface 15. The pitch is taken to be the angle of the slope relative to an axis which is normal to the longitudinal axis of the shaft and as shown as line x-x in FIG. 2.

The pitch of guide surface 15 as depicted is constant along a length of the guide surface from outer edge 17 to the inner edge 18.

Figure 4:
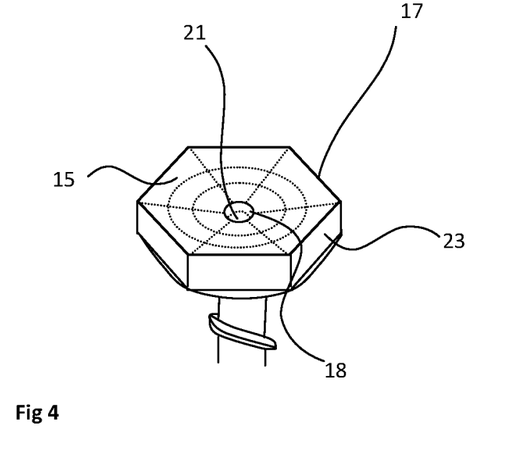
FIG. 4 is a side elevational view of the head of an embodiment of a fiducial marker.
Figure 5:
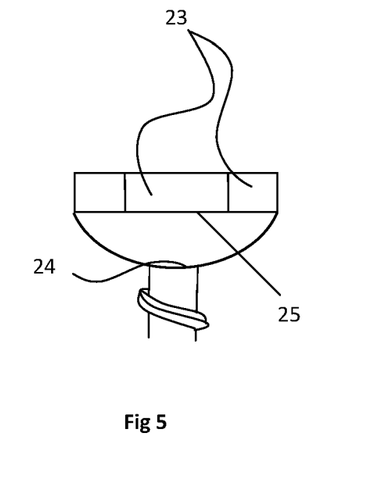
FIG. 5 is a side view of the head of FIG. 4.
Figure 6:
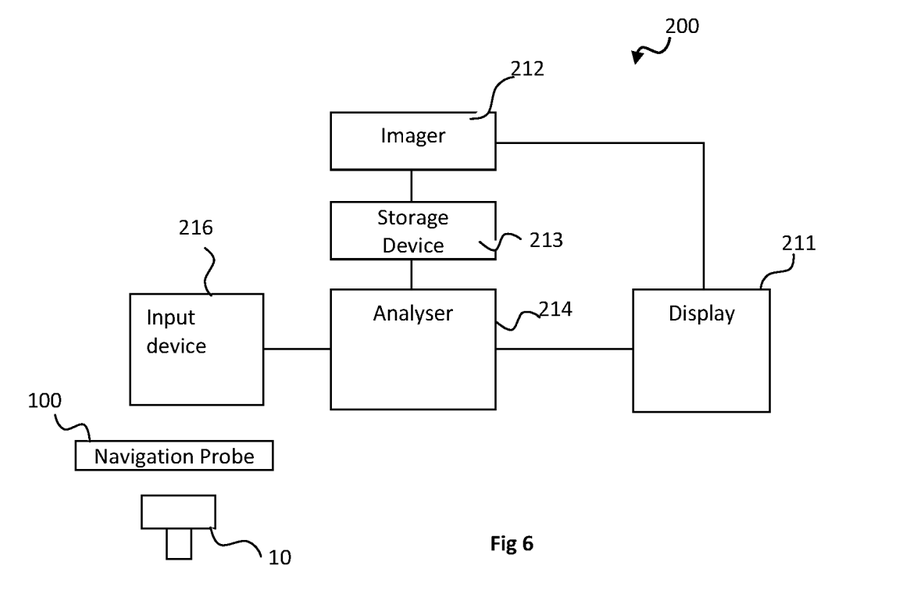
FIG. 6 is a flow chart illustrating a navigation system using the fiducial markers herein disclosed.

As depicted in FIGS. 4 and 6, head 11 has at a plurality of outer sidewalls 23. As shown in FIG. 4, the head has six identical sidewalls 23 to form a hex nut structure. The six outer sidewalls 23 form a driver feature for marker 10 by which a complementary socket driver grips the sidewall and allows a surgeon to insert the marker into a bone, or remove the marker from the bone.

Lower surface 13 of head 11 includes a central portion 24 substantially aligned longitudinally with well 16. This central portion 24 comprises the lowest point on lower surface 13. Further, shaft 14 extends from central portion 24 of the lower surface 13.

Lower surface 13 curves outwardly from central portion 24 to a junction 25 with outer sidewall 23. The rate of curvature of the lower surface is relatively constant.

Base 21 of well 16 aligns with junction 25. Outer sidewalls 23 are visible to a CT or other scanner, the sidewall being distinct from the lower curved surface 13. Base 20 aligns with junction 25 to provide visual comparison of the location of navigation probe 100 in relation to fiducial marker 10 on the navigation system's imaging screens. If the probe is accurately shown on a screen it will appear to be centrally positioned on the head and at the same depth as junction 25.

Shaft 14 is threaded along its length from a first end 26 to a second bone cutting end 27.

When used in a broader navigation system, the markers as mentioned may provide a check of the accuracy of the imaging.

The depicted, system 200 in FIG. 6 is designed to aid a surgeon or surgical team performing corrective spinal surgery. The system 200 comprises a computer monitor 211 that serves to display CT images taken of a patient's spine by a CT imager 212. The images displayed on display 211 are stored in a suitable data storage device 213.

The system further comprises an analyser 214 in the form of a computer processor. The analyser 214 is designed to compare the CT image provided by the imager 212 with the position of one or more fiducial markers 10 positioned on the patient. The position of the one or more markers 10 is determined using a surgical navigation probe 100 which is brought into contact with the one or more markers 10. The positional data from the probe 100 is provided through an input device 216 to the analyser 214 which in turn provides an output of said comparison to the display device 211. The use of the probe allows the analyser 214 to generate correctional data so allowing for correctional alignment of the displayed CT image to match with the actual position of the one or more markers 10 on the patient.

Figure 8A:
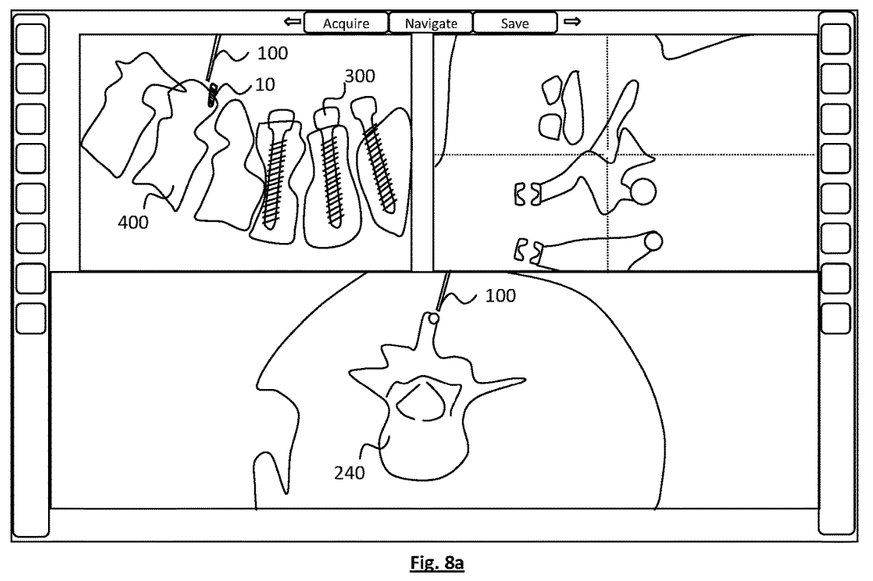
FIGS. 8a and 8b are representations of images taken during a procedure.
Figure 8B:
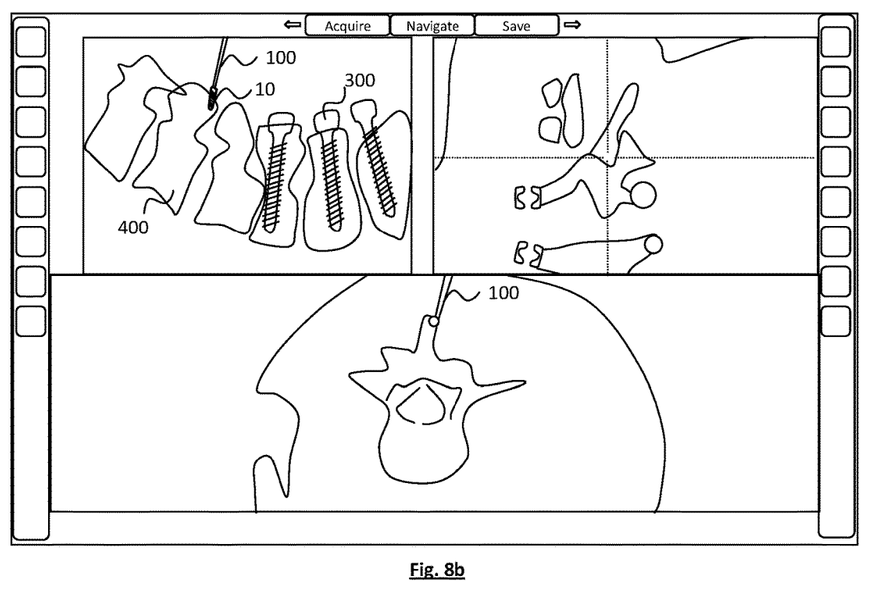

To position the one or more fiducial markers 10, the surgeon first exposes bony anatomy of the spine 240, posteriorly, laterally, obliquely, or anteriorly, at the desired levels. FIG. 8 provides an illustrative depiction of this. A fiducial marker 10 can then be mounted to a piece of bone away from the area to be resected or operated thereon, usually the next vertebra up or down the spine 240 and usually on the spinous process in a posterior approach.

One or more markers 10 and/or probe 100 can include reflective components, such as reflective balls 220. The reflective components can be designed to reflect light of a particular frequency, for example infrared (IR), with a navigation device, such as IR camera 202, having a capability to remotely detect the position of the markers, probe and other instruments being then part of the system. In use, the IR camera is pointed at the whole operative site, including the surgical marker(s) clamped or mounted to bone.

The position of a first marker 10 may be determined using the reflective components 220 and/or through being probed, and initial registration of the displayed image may therefore be made using the first marker 10. A CT scan can then be taken. This can be achieved through use of a mobile CT scanner that is brought into the operating theatre. In taking the CT scan, the aim is to show all of the desired operative levels as well as the fiducial markers.

The CT scanner can be connected or viewed by the IR camera and subsequent CT images obtained in all three planes can be looked at simultaneously on three separate regions or windows of the display 11. These images typically show the patient as they are lying on the operating table and as depicted in FIG. 8, fiducial marker 10 can be seen in the bone. Furthermore, probe 100 may have one or more reflective markers 220 as described herein and can be used by the surgeon such that it effectively points at various parts of the anatomy. Using the IR camera, the location of probe 100 relative to the patient may be monitored and superimposed over the CT images of the patient's anatomy.

Figure 7:
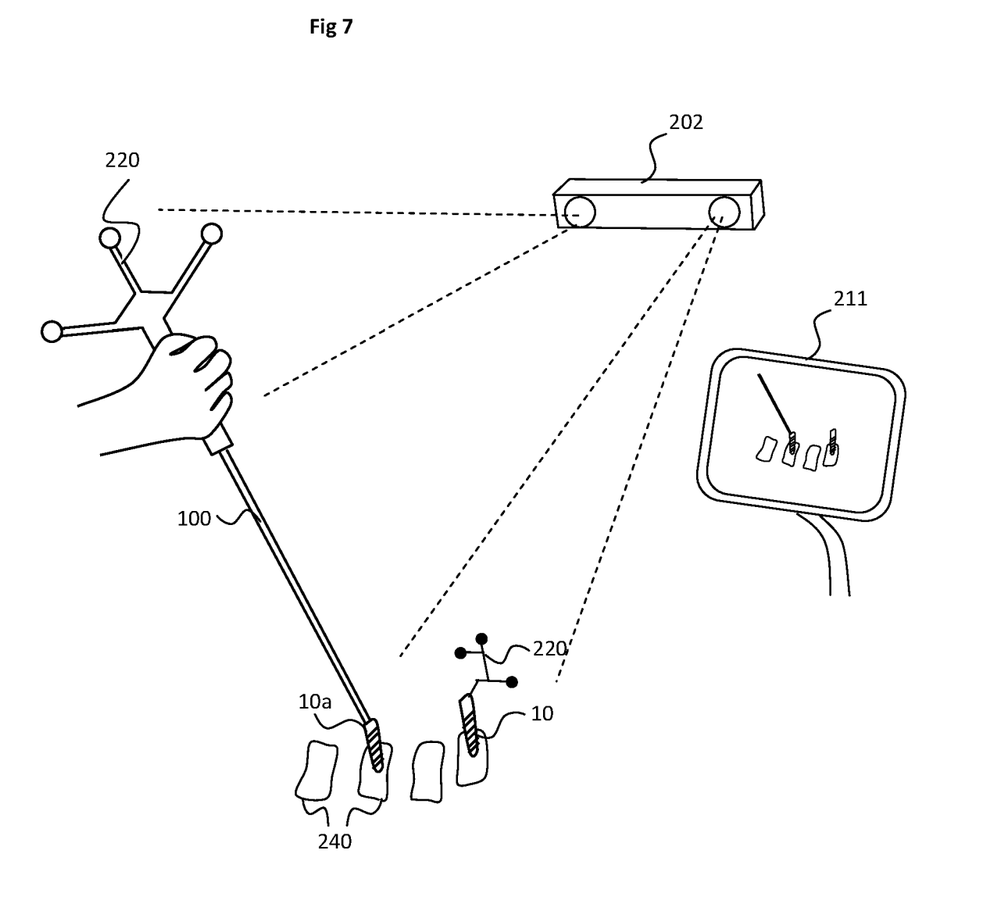
FIG. 7 is a schematic representation of use of a probe and the fiducial markers as herein disclosed in a navigation system.

An illustration of a surgeon manipulating probe 100, in order to probe the position of a fiducial marker 10a located in the spine 240 of a patient's body, in the field of view of an IR camera 202, is provided in FIG. 7.

The system can be used to identify the correct placement point for one or more pedicle screws 300, as well as the correct angle, and depth, to drill for them. As the pedicles of the vertebra are drilled, probe 100 can also be inserted into the drill hole to check its location and orientation. The planned screw size can also be superimposed, rather than just the line of the probe, to ensure the screw diameter and length do not exceed the available space.

During this procedure, fiducial markers 10 can be used, from time to time, to check the accuracy of the navigation. Because the markers are in situ when the CT scan is taken, they show on the CT images. Probe 100 as superimposed on the displayed images should then be shown touching exactly onto the heads of the scanned markers 10 when the probe 100 is touched onto the heads of the actual screws by the surgeon. However, this is often not the case with the screws appearing to be 1 or more millimetres away from the position of the probe when viewed on the display, despite the fact the probe is placed exactly in head 11, or as exactly as the head 11 design allows, as shown in FIG. 8a. This "offset" could require the surgeon to estimate a correction for the image shown for the other areas of anatomic interest, such as the pedicle of the vertebra.

The system as described herein provides the surgeon or surgical team with a means of correcting for such offsets when they occur. Although not depicted, at least three fiducial markers 10 can be positioned to the patient, each on a different plane to that of the others. The use of at least three fiducial markers 10 can ensure that the CT image can be realigned in at least three axes/planes, so ensuring an appropriate three dimensional image of the anatomy of the patient. At least three fiduciary screws may be positioned on each segment (e.g., on each vertebra). As the spine consists of multiple intercalated segments with intrinsic abilities for movement in any plane at any time point, the use of three fiduciary markers per segment may allow ultimate control of subsequent image manipulation and hence navigation.

In one embodiment, the analyser 214 of the system 200 can make an initial determination of the position of the three fiducial markers 10 and so form a three dimensional image. For example, the analyser can in effect create a three dimensional solid based on the initial determination of the three fiduciary screws. The surgeon can then use 100 to physically touch the actual fiducial markers 10 to generate positional data. The analyser 214 can then use the positional data provided by this action to form a corrected three dimensional solid and then manipulate or align the CT image on the display to the actual location of the body, thus providing a form of registration or re-registration of the image and the patient's body. The corrected image is shown in FIG. 8b.

The features of the fiducial markers 10 having a guide surface 15 and a well 16 allow a surgeon to easily and reliably contact the marker with probe 100. The slope of the guide surface 15 guides the tip of probe 100 towards and into well 16. The dimensions of well 16 are such that the tip of probe 100 sits within the well and is not easily dislodged.

Figure 9:
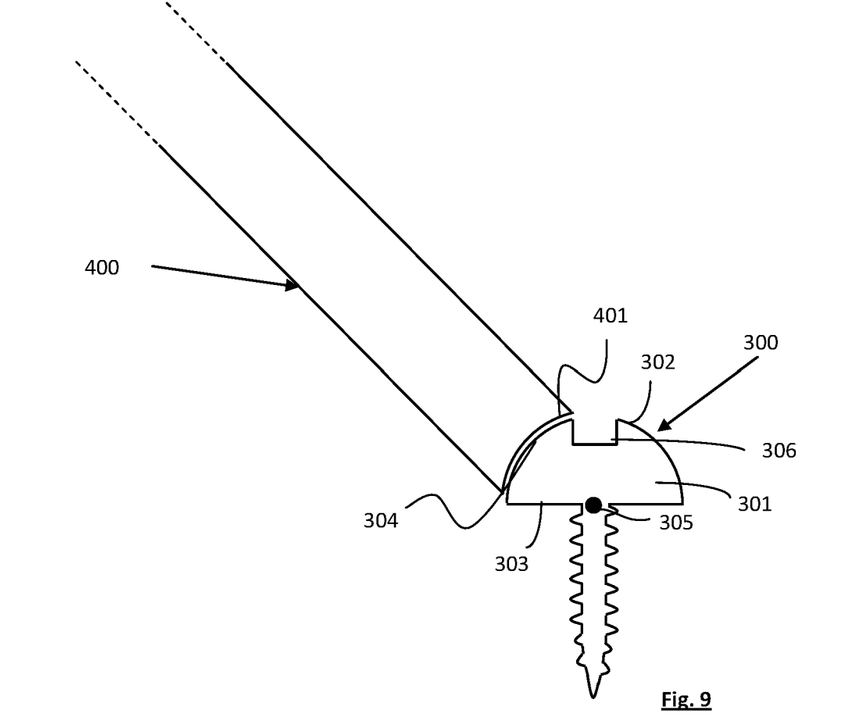
FIG. 9 is a cross sectional view of a fiducial marker and navigation probe according to a further embodiment.

FIG. 9 depicts a further embodiment of a fiducial marker 300 which has a head 301 with an upper surface 302 and a lower surface 303. Upper surface 302 includes a guide surface 304 for receiving a navigation probe 400. As shown, guide surface 304 comprises a convex surface which engages with a complementary concave surface 401 of navigation probe 400. Specifically, in this embodiment, through monitoring using a navigation system the positioning of the concave surface 401 of the navigation probe 400 and the orientation of the probe 400 axis, the axis in free space along which the spherical centre 305 of the fiducial marker 300 lies can be determined. Moreover, through knowledge of the constant distance between the concave surface 401 and the spherical centre 305 of the fiducial marker 300 (which is the substantially same as the radius of the spherical top surface of the fiducial marker 300 when the concave surface 401 is engaged with the guide surface 304), the location of the spherical centre 305 can be identified.

As may be appreciated from the embodiment shown in FIG. 9, for example, the concave surface 401 may be positioned to align with other parts of the upper surface 302 which would therein comprise the guide surface for the probe 400.

Fiducial marker 300 also includes a hex drive recess 306 to allow the marker to be driven into a bone of a patient.

Figures 10A, 10B:
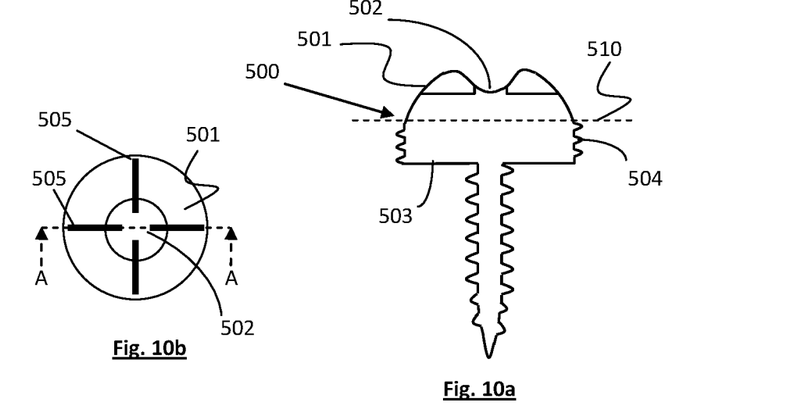

FIG. 10a shows an embodiment of a fiducial marker 500 wherein upper surface 501 includes dimple 502. This marker 500 may be used with either of the probe types depicted as 100 and 400. That is, dimple 502 may act as a guide surface to guide probe 100. Further, the hemispherical nature of at least part of the upper surface 501 allows a probe having a concave tip such as shown in FIG. 9a to be brought into abutment with the upper surface 501.

A region of the upper surface adjacent to its join with lower surface 503 includes a screw thread 504. This allows the head to be screwed into a bone. An imaginary upper bony surface is shown in FIG. 9b as dashed line 510 which depicts the positioning of the marker 500 once positioned in the bone.

A top plan view of marker 500 is shown in FIG. 10b. In this embodiment, cross screws 505 are provided on upper surface 501 to receive a driver to allow the marker 500 to be implanted in a bone.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention claimed is:

1. A fiducial marker system comprising:
   a fiducial marker;
   a navigation probe; and
   a navigation system configured to register or re-register a position of the fiducial marker on the navigation system when a tip of the navigation probe is in contact with the fiducial marker,
   wherein the fiducial marker comprises:
   a head having an upper surface and a lower surface; and
   a shaft extending along a longitudinal axis from the lower surface of the head;
   wherein the upper surface has a sloped guide surface and a centrally positioned well configured to receive at least the tip of the navigation probe,
   wherein the sloped guide surface slopes downwardly and inwardly from an outer edge of the head to an uppermost edge of the well such that the sloped guide surface is configured to guide the tip of the navigation probe towards and into the well, the uppermost edge of the well defining an inner edge of the sloped guide surface;
   wherein the well is hemispherical and has a sidewall sloping downwardly and inwardly from the uppermost edge of the well to a closed base of the well, wherein the sidewall of the well slopes at a pitch that is steeper than a pitch of the sloped guide surface.

2. The fiducial marker system of claim 1, wherein the fiducial marker is a pedicle screw.

3. The fiducial marker system of claim 1, wherein a diameter of the well is less than 30% of a diameter of the head.

4. The fiducial marker system of claim 1, wherein the upper surface and the lower surface are connected by at least one outer sidewall.

5. The fiducial marker system of claim 1, wherein the sloped guide surface slopes at a constant pitch.

6. The fiducial marker system of claim 1, wherein the navigation probe comprises an elongate body, the tip of the navigation probe being at one end of the elongate body and having a convex or spherical shape.

7. The fiducial marker system of claim 1, wherein a thread of the shaft has a reduced depth adjacent to the lower surface of the head relative to the remainder of the thread.

8. A fiducial marker comprising:
   a head having an upper surface and a lower surface; and
   a shaft extending along a longitudinal axis from the lower surface of the head;
   wherein the upper surface has a sloped guide surface and a centrally positioned well,
   wherein the sloped guide surface slopes downwardly and inwardly from an outer edge of the head to an uppermost edge of the well, the uppermost edge of the well defining an inner edge of the sloped guide surface, and wherein the well is hemispherical and has a sidewall sloping downwardly and inwardly from the uppermost edge of the well to a closed base of the well, wherein the sidewall of the well slopes at a pitch that is steeper than a pitch of the sloped guide surface.

\* \* \* \* \*